US010695719B2

(12) United States Patent
Wilson et al.

(10) Patent No.: US 10,695,719 B2
(45) Date of Patent: Jun. 30, 2020

(54) PRODUCING AMMONIUM CARBAMATE AND REDUCING NITROGEN OXIDES

(71) Applicant: LOUGHBOROUGH UNIVERSITY, Leicestershire (GB)

(72) Inventors: Jonathan Wilson, Leicestershire (GB); Graham Hargrave, Leicestershire (GB)

(73) Assignee: LOUGHBOROUGH UNIVERSITY, Leicestershire (GB)

(*) Notice: Subject to any disclaimer, the term of this patent is extended or adjusted under 35 U.S.C. 154(b) by 0 days.

(21) Appl. No.: 16/465,825

(22) PCT Filed: Dec. 1, 2017

(86) PCT No.: PCT/EP2017/081246
§ 371 (c)(1),
(2) Date: May 31, 2019

(87) PCT Pub. No.: WO2018/100187
PCT Pub. Date: Jun. 7, 2018

(65) Prior Publication Data
US 2020/0023312 A1 Jan. 23, 2020

(30) Foreign Application Priority Data

Dec. 1, 2016 (GB) .................................. 1620445.5
May 30, 2017 (EP) .................................... 17173506

(51) Int. Cl.
*B01D 53/90* (2006.01)
*B01D 53/94* (2006.01)
(Continued)

(52) U.S. Cl.
CPC ......... *B01D 53/90* (2013.01); *B01D 53/8631* (2013.01); *B01D 53/9431* (2013.01);
(Continued)

(58) Field of Classification Search
CPC ........... B01D 53/9409; B01D 53/9418; B01D 53/9422; B01D 2251/206; B01D 2251/2062; B01D 2257/402; B01D 2258/012; F01N 3/206; F01N 3/208; F01N 2240/25; F01N 2570/14; F01N 2570/145; F01N 2610/01; F01N 2610/02; F01N 2610/10; F01N 2610/11; F01N 2610/1406
See application file for complete search history.

(56) References Cited

U.S. PATENT DOCUMENTS 8,844,269 B2 9/2014 Henry et al.
2001/0053342 A1 12/2001 Marko et al.
(Continued)

FOREIGN PATENT DOCUMENTS

CN 103437865 B 12/2015
EP 0524953 A1 2/1993
(Continued)

OTHER PUBLICATIONS

PCT/EP2017/081246, International Search Report dated Mar. 14, 2018.
(Continued)

*Primary Examiner* — Timothy C Vanoy
(74) *Attorney, Agent, or Firm* — Meunier Carlin & Curfman LLC (57) ABSTRACT

A process for reducing nitrogen oxides in an exhaust stream, such as a vehicle exhaust stream, and apparatus for carrying out the process. The process comprises providing a first composition comprising aqueous urea, a second composition comprising ammonium carbamate and an exhaust stream comprising nitrogen oxides. A process for producing the ammonium carbamate is also provided. The second composition may be introduced into the exhaust stream (10) when the exhaust stream has a temperature below a threshold temperature and the first composition may be introduced into the exhaust stream when the exhaust stream has a temperature at or above the threshold temperature.

20 Claims, 8 Drawing Sheets

(51) Int. Cl.
  *B01D 53/86* (2006.01)
  *C01B 21/12* (2006.01)
  *C07C 269/04* (2006.01)
  *F01N 3/20* (2006.01)

(52) U.S. Cl.
  CPC ............ *C01B 21/12* (2013.01); *C07C 269/04* (2013.01); *F01N 3/208* (2013.01); *B01D 2251/2067* (2013.01); *B01D 2257/404* (2013.01)

(56) References Cited

U.S. PATENT DOCUMENTS

| | | | |
|---|---|---|---|
| 2016/0153335 A1 | 6/2016 | Itoh et al. | |
| 2016/0167974 A1* | 6/2016 | Novek | C07C 273/04 429/50 |
| 2019/0234283 A1* | 8/2019 | Adelman | F01N 3/035 |

FOREIGN PATENT DOCUMENTS

| | | |
|---|---|---|
| EP | 1918274 A1 | 5/2008 |
| GB | 756934 A | 9/1956 |
| GB | 757016 A | 9/1956 |
| IL | 49998 A | 11/1979 |
| IT | 1037576 B | 11/1979 |
| WO | 8806569 A1 | 9/1988 |
| WO | 9606674 A1 | 3/1996 |
| WO | 9956858 A2 | 11/1999 |
| WO | 03010089 A1 | 2/2003 |

OTHER PUBLICATIONS 17173506.1, Extended European Search Report dated Apr. 1, 2018.
GB1620445.5, Patents Act 1977: Search Report under Section 17(5), dated Jan. 27, 2017.
GB1620445.5, Patents Act 1977: Search Report under Section 17(6), dated Apr. 25, 2017.

* cited by examiner

PRODUCING AMMONIUM CARBAMATE AND REDUCING NITROGEN OXIDES

This invention relates to processes for producing ammonium carbamate and for reducing nitrogen oxides (NOx) in an exhaust stream, and to apparatus for carrying out the processes.

Vehicle engines manufactured for sale in Europe must abide by a set of stringent emission targets laid out by the European Commission which covers a range of possible pollutants. Nitrogen oxides (NO and $NO_2$, referred to collectively as NOx) are one such emission. The transport sector is the largest contributor to NOx emissions in the European Union (EU), accounting for 46% of total emissions in 2013. As such the emission limits for NOx are being reduced and becoming increasingly difficult to meet. Similar legislation exists in many other jurisdictions, such as China, India and Japan.

A selective catalytic reduction (SCR) system can be employed to reduce NOx emissions. The SCR system has been used in power plants for some time and uses ammonia as a reductant which reacts with NOx in the presence of a catalyst and produces nitrogen and water. EP0524953 B1 (Fuel Tech) describes a utility boiler where a first treatment agent (urea or ammonia) is introduced into an effluent stream at a first effluent temperature zone (e.g. 982° C. to 1149° C.) and a second treatment agent (ammonium carbamate) is then introduced into the effluent at a different temperature zone (e.g. 704 to 982° C.).

The use of SCR in vehicles is a more recent development and employs an ammonia precursor in place of ammonia because ammonia is impractical to refuel and potentially unsafe to carry.

US2001/0053342 describes a device where gaseous ammonia is made available by heating a solid storage medium in a container. The storage medium binds ammonia by physical and/or chemical absorption. The container is large (e.g. 10 liters) in order to store enough ammonia to last for the period between vehicle services.

For vehicles, there has been an industry-wide adoption of an ammonia precursor consisting of 32.5% urea and 67.5% deionized water. This aqueous urea solution is standardised as AUS32 (aqueous urea solution) in ISO 22241. It is commonly known as AdBlue® or diesel exhaust fuel (DEF).

AdBlue® is injected directly into a hot exhaust stream where, due to the elevated temperatures, it decomposes producing ammonia. However, a temperature of 350° C. within the exhaust stream is desirable for full decomposition. Therefore periods of operation can exist where temperatures are insufficient to fully support decomposition to ammonia. SCR operation must be ceased since the urea can produce alternative decomposition products, which form deposits. These deposits can build up within the exhaust system increasing back pressure and leading to engine failure. Additionally, due to its high water content AdBlue® is prone to freezing.

US2016/153335 A1 (Toyota) describes an exhaust gas purification apparatus of an internal combustion engine that includes an SCR NOx catalyst, and a tank that stores aqueous urea, a hydrolysis catalyst and a heater. The hydrolysis catalyst is heated and urea is hydrolysed on the catalyst and passes into the exhaust passage.

The present invention seeks to overcome one or more of the drawbacks of the current processes for reducing nitrogen oxides in exhaust streams.

According to a first aspect of the present invention there is provided a process for reducing nitrogen oxides (NOx) in an exhaust stream, the process comprising
providing a first reservoir having a first composition therein, the first composition comprising an aqueous solution of urea;
transferring a portion of the first composition along a flow path, the flow path being in communication with a second reservoir;
heating the portion of the first composition to produce a mixture comprising ammonia, carbon dioxide and water, the heating taking place in the flow path or the second reservoir;
cooling the mixture to generate a second composition, the cooling taking place in the flow path or in the second reservoir and the second composition comprising an aqueous solution of ammonium carbamate; and
introducing the second composition from the second reservoir into an exhaust stream comprising nitrogen oxides.

Ammonium carbamate decomposes on heating to form ammonia and the resulting ammonia reduces the NOx in the exhaust stream. Ammonium carbamate decomposes to form ammonia very quickly and at low temperatures. This is demonstrated in the examples.

As such, ammonium carbamate does not form deposits. Moreover the present invention also allows greater control of ammonia delivery. Rapid decomposition times shorten the delay between injection command and ammonia delivery. This allows a control system capable of dealing with rapid NOx transients. (i.e. below 1 second).

Hence the present invention enjoys the benefits of AdBlue®, which is readily available and safe to store on a vehicle, together with the benefits of ammonium carbamate including its ease of decomposition.

The process of the present invention requires the production of ammonium carbamate in situ. As discussed below, it is not practical or safe to employ ammonium carbamate solution as a direct replacement for AdBlue®. It would be necessary to transport large volumes of the solution, which is technically difficult and potentially unsafe.

Instead generation of ammonium carbamate in situ allows small quantities to be prepared, stored, and used as needed.

This invention provides particular benefits relative to the prior art process described in US2014/0214963. US'963 discloses the use of a canister of metal-ammine salts, which offer a solid storage medium for ammonia. The metal-ammine acts as a "reservoir" for the ammonia and cannot be generated in situ.

The process of the present invention allows a high NOx strategy to be employed, e.g. to allow an engine to run at high temperature and thereby produce less $CO_2$. The ammonium carbamate that is generated in situ can be used alone or with support from the first composition (e.g. AdBlue®) to increase the total amount of ammonia it is possible to deliver to the exhaust stream. This will allow an SCR system to have a greater NOx conversion capacity and therefore allow a greater engine output of NOx.

An additional benefit of the present invention is that the second composition is volatile and rapidly generates ammonia. This effervescent process acts as a mild mechanical cleaning process to remove deposit growth on surfaces. As such, the invention also resides in the use of ammonium carbamate to remove deposits.

Moreover, ammonium carbamate has benefits even relative to ammonium carbonate and ammonium bicarbonate. Ammonium carbamate decomposes at lower temperature than both ammonium carbonate and ammonium bicarbonate, as shown in the examples.

Ammonium Carbamate as the Sole Reducing Agent

It will be appreciated that both the first composition and the second composition can be employed to generate ammonia and thereby reduce NOx. However, in some circumstances is may be beneficial to employ only the second composition.

In this way, there is no need to include hardware to inject and decompose urea to form ammonia, which simplifies the system architecture. This is especially good for applications having space constraints such smaller vehicles (e.g. cars), generators (e.g. back-up generators) and cooling engines.

It is also very useful for low temperature cycles (e.g. vehicles which travel at low speed and/or stop frequently, such as buses). In such cases, using the first composition (aqueous urea) as a source of ammonia for reducing NOx has drawbacks as discussed in more detail below.

In embodiments the second composition (comprising ammonium carbamate) is the sole reducing agent for NOx. i.e. the first composition is employed only to generate the second position, and not to reduce NOx.

Threshold Temperature

In embodiments the second composition is introduced into the exhaust stream when the exhaust stream has a temperature below a threshold temperature and the first composition is introduced into the exhaust stream when the exhaust stream has a temperature at or above the threshold temperature.

Both urea and ammonium carbamate decompose on heating to form ammonia and the resulting ammonia reduces NOx. Ammonium carbamate decomposes to form ammonia more readily than urea. Hence, we propose the use of ammonium carbamate to generate ammonia at lower temperatures and urea at higher temperatures. An advantage of the process is that NOx can be reduced even when present in a low temperature exhaust stream i.e. a cold-start process. The process has a significant environmental impact. Not only does the process reduce NOx, it may also have a positive impact on other engine emissions such as particulate matter (PM) and $CO_2$ since the increased ability to treat NOx allows for more efficient engine operation.

The suitability of the first and second compositions for reducing NOx depends on the temperature of the exhaust stream. The first composition (comprising urea) may be more appropriate at higher temperatures and the second composition (comprising ammonium carbamate) is more appropriate at lower temperatures.

The skilled person can select the threshold temperature depending on the circumstances. The skilled person will appreciate that the threshold temperature can be selected depending on a number of familiar factors including the amount of NOx and other emissions that he is willing to tolerate, the quantities of the first and second compositions that are available, the amount of deposition (from urea) that he is willing to tolerate, any additional components present in the first and second compositions, and the operating conditions.

For example, an exhaust stream temperature of at least 350° C. is desirable for full decomposition of AdBlue® to form ammonia. Deposits are likely to form when the temperature is lower. In particular, a practical implementation of the invention with direct AdBlue® dosing is challenging at temperatures below 190° C. In general, when using AdBlue®, deposits may need to be considered at temperatures below 250° C. Therefore, if AdBlue® is employed as the first composition the skilled person may select a threshold temperature of at least 250° C., or of at least 275° C., or of at least 300° C.

In one series of embodiments the threshold temperature is at least 100, 150, 200, 230, 250, 270, 300, 350 or 400° C. and/or no more than 1000, 800, 600, 400, 200 or 150° C. It may be that the threshold temperature is selected from the range of from 100 to 600° C., or from 100 to 500° C., or from 100 to 450° C., or from 100 to 400° C. It may be that the threshold temperature is selected from the range of from 150 to 500° C., or from 150 to 450° C., or from 150 to 400° C. It may be that the threshold temperature is selected from the range of from 200 to 500° C., or from 200 to 450° C. In a particular embodiment, the threshold temperature is selected from the range 200 to 400° C. In other embodiments, it may be that the threshold temperature is selected from the range of from 250 to 500° C., or from 250 to 450° C., or from 250 to 400° C.

The process may be employed such that only the first composition or only the second composition is introduced into the exhaust stream at a given temperature i.e. the threshold temperature can act as a cut-off. In some embodiments the first composition is only introduced into the exhaust stream when the exhaust stream has a temperature at or above the threshold temperature. In some embodiments the second composition is only introduced into the exhaust stream when the exhaust stream has a temperature below the threshold temperature.

Alternatively the process may be employed such that both of the first composition and the second composition are introduced into the exhaust stream at a given temperature. In some circumstances the skilled person may have to consider that certain deposits can be formed by AdBlue® even at temperatures in excess of 350° C. Therefore dosing the second composition at these times may be advantageous even if a lower threshold temperature is specified.

In some circumstances a gradual change from the second composition to the first composition as the temperature of the exhaust stream increases may be beneficial. Such an approach would avoid the risk of no reducing agent being available for even a short period of time.

In embodiments the first composition is only introduced into the exhaust stream when the exhaust stream has temperature (the exhaust stream temperature)
(i) at or above the threshold temperature; or
(ii) no more than 100, 50, 20 or 10° C. below the threshold temperature.

In embodiments the second composition is only introduced into the exhaust stream when the exhaust stream has temperature (the exhaust stream temperature)
(i) below the threshold temperature; or
(ii) no more than 100, 50, 20 or 10° C. above the threshold temperature. Alternatively, the second composition may be introduced into the exhaust stream regardless of the temperature.

It will be understood that it is necessary to know the temperature of the exhaust stream in order to determine whether the first composition and/or the second composition should be introduced. The temperature could be measured by means of a dedicated sensor. Alternatively an approximate temperature might be inferred from the conditions. In embodiments the process additionally comprises measuring the temperature of the exhaust stream. The temperature of the exhaust stream may be compared to the threshold temperature and the first composition and/or the second composition can be selected for introduction into the exhaust stream. In embodiments the process comprises measuring the temperature of the exhaust stream and reporting the value to a programmable electronic control unit (ECU). The ECU can be programmed to release the first composition and/or the second composition into the exhaust steam, e.g. by means of a dosing valve.

First Composition

Urea has the formula (I):

(I)

The first composition is an aqueous solution of urea and is in liquid form at standard ambient temperature and pressure (SATP). The first composition comprises water and urea: $CO(NH_2)_2$. In one such embodiment the first composition consists essentially of urea and water, e.g. AdBlue® (aqueous urea solution, standardised to AUS32, also known as a diesel engine fuel (DEF)). There is already an existing market acceptance for AdBlue® as an ammonia precursor and an extensive distribution network.

In one series of embodiments the first composition comprises at least 5, 10, 15, 20, 25, 30, 35, 40, 45 or 50 wt % urea/or no more than 80, 70, 60, 50, 40, 30, 20 or 10 wt % urea. The balance may be water.

In one embodiment the first composition comprises 30 to 35 wt %, 31 to 34 wt %, 32 to 33 wt % or approximately 32.5% urea, with the balance being water. The commercially available product AdBlue® consists of 32.5 wt % urea and 67.5 wt % water. This is said to be correspond closely to a eutectic mixture. In a preferred embodiment the first composition is AdBlue®.

The first composition may be introduced into the exhaust stream in any conventional way e.g. by injection of the aqueous solution.

Second Composition

The second composition comprises ammonium carbamate: $H_2NCO_2NH_4$. Ammonium carbamate is the ammonium salt of carbamic acid ($NH_2CO_2H$) and has the formula (II)

Ammonium carbamate decomposes to produce ammonia and carbon dioxide. Decomposition can occur as early as 25° C., meaning that the reduction of NOx can occur even at low temperatures (c.f. 350° C. for AdBlue®). This is a benefit at low temperature but leads to difficulties at higher ambient temperatures, since sealed storage is required.

Ammonium carbamate dissolves in water to provide a solution of ammonium ions and carbamate ions. The use of ammonium carbamate solution for the selective catalytic reduction of NOx is known (WO96/06674). However, it would not be practical to employ ammonium carbamate solution as a direct replacement of AdBlue®, especially in vehicle engines.

A benefit of AdBlue® is that it is very stable at ambient temperatures; it is stored in a tank in a vehicle and refilled as necessary. A passenger car may have a tank that holds 15 to 20 liters of AdBlue®. A heavy goods vehicle would have a much larger tank. It would not be safe or practical to carry such high volumes of ammonium carbamate solution. The ammonium carbamate would decompose to form ammonia, which is toxic and also flammable in sufficient quantities. Therefore a specifically designed tank would be required to maintain the vapour pressure and prevent sublimation. WO96/06674 confirms that shipping of the aqueous solution is impractical and recommends shipping the ammonium carbamate in dry form and then dissolving it on the site of the NOx reduction process.

The second composition is an aqueous composition i.e. a solution of the ammonium carbamate in liquid water. In embodiments the second composition consists of ammonium carbamate and water, optionally with dissolved ammonia.

In embodiments the second composition comprises at least 5, 10, 15, 20, 25, 30, 35, 40, 45 or 50 wt % ammonium carbamate and/or no more than 70, 60, 50, 40, 45, 30, 35, 20 or 10 wt % ammonium carbamate. The balance may be water.

In embodiments the second composition comprises from 25 to 45 wt %, from 30 to 44 wt %, from 33 to 43 wt % or approximately 42 wt % ammonium carbamate. When the ammonium carbamate is produced in situ from AdBlue® (32.5 wt % urea and 67.5 wt % water), the resulting ammonium carbamate solution comprises approximately 42.25 wt % ammonium carbamate (assuming complete conversion).

The second composition may be introduced into the exhaust stream in any conventional way e.g. by injection of the aqueous solution.

Reduction of NOx

The urea solution and the ammonium carbamate solution may each produce ammonia, which reduces NOx in the exhaust stream. In embodiments the exhaust stream comprises a reduction chamber having a selective catalytic reduction (SCR) catalyst therein.

Applications

The process comprises reducing NOx in an exhaust steam from a combustor, such as an internal combustion engine. The combustor may be stationary (e.g. a utility boiler, a natural gas generator, a gasoline generator or diesel generator) or mobile (e.g. a vehicle). The process is especially useful for on highway and off highway vehicles which currently employ SCR reduction of NOx.

In embodiments the process comprises reducing NOx in a vehicle exhaust stream. i.e. the process comprises reducing NOx in a vehicle exhaust stream where the ammonium carbamate is prepared in situ i.e. on vehicle.

The process is not limited to diesel engines and can also be used for gasoline. The process of the present invention enables an SCR system designed for gasoline since the exhaust temperatures are likely to be lower than that of a comparable diesel engine. The process may allow a decrease in NOx emission limits or an engine no longer running at conditions applicable to existing gasoline after-treatment.

The process is applicable to dual fuel vehicles or generators.

The process is especially useful for hybrid electric vehicles i.e. an electric vehicle that combined an internal combustion engine with an electric propulsion system. The internal combustion engine may be cold, even if the vehicle has been running using the electric system for some time. In embodiments the vehicle exhaust stream is a hybrid electric vehicle (e.g. diesel hybrid or gasoline hybrid) exhaust stream.

According to a second aspect of the present invention there is provided a process for the preparation of ammonium carbamate comprising providing a first reservoir having an aqueous solution of urea therein;

transferring a portion of the aqueous solution of urea along a flow path, the flow path being in communication with a second reservoir;

heating the portion of the aqueous solution of urea to produce a mixture comprising ammonia, carbon dioxide and water;

cooling the mixture to generate an aqueous solution of ammonium carbamate;

wherein each of the heating and the cooling takes place in the flow path or in the second reservoir.

It will be understood that the aqueous solution of urea and the aqueous solution of ammonium carbamate may constitute the first and second compositions of the first aspect of the invention. In embodiments only a portion of the aqueous urea solution is converted into ammonium carbamate; a volume of aqueous urea solution remains within the first reservoir.

In one example, the process of the present invention provides 8 g of ammonium carbamate solution per minute. This is sufficient to reduce 2.8 g NOx.

WO96/06674 describes a method for the selective catalytic reduction of NOx where a solution of ammonium carbamate is employed to generate ammonia. The ammonium carbamate is said to be produced in equipment conventional for urea synthesis. It will be understood that the present process is carried out on a smaller scale. Hence, the volumes employed will be much smaller than in the industrial production of urea.

The first reservoir may correspond to a conventional AdBlue® tank on a vehicle. In embodiments the first reservoir has a volume of no more than 500, 200, 100, 50, 30 or 20 liters and/or at least 10, 20 or 50 liters. In embodiments the first reservoir has a volume of 10 to 100 liters.

The second reservoir stores the aqueous ammonium carbamate that is produced. Hence a portion of the aqueous solution of urea is transferred from the first reservoir, along the flow path, to the second reservoir and may be converted to ammonium carbamate on the way or in the second reservoir. As discussed above, it may not be safe or practical to store large volumes of aqueous ammonium carbamate. In embodiments the second reservoir has a volume of no more than 10, 8, 5, 3, 2, 1 or 0.5 liters and/or at least 0.05, 0.1, 0.2, 0.5, or 1 liters.

In embodiments the first reservoir has a greater volume than the second reservoir. In embodiments, the volume of the first reservoir is at least 5, 10, 20, 50 or 100 times greater than the volume of the second reservoir.

In embodiments the portion of the aqueous urea is heated by an electrical heater.

In embodiments the portion is heated by a heat-exchanger, e.g. a heat-exchanger in communication with an exhaust stream, engine coolant or an electrical heater. It is an advantage of the present process that the ammonium carbamate can be produced when an exhaust stream is hot, using energy that would otherwise be wasted. This means that ammonium carbamate solution is available in the second reservoir for subsequent use.

In embodiments the heating comprises heating the portion of the aqueous urea solution to a temperature of at least 100, 150, 200, 250, 300, 350 or 400° C. and/or no more than 1000, 800, 600 or 500° C. Higher temperatures minimise the generation of alternative decomposition products which cause deposits.

In embodiments the heating is carried out at or above atmospheric pressure. In one embodiment heating may be carried out in a sealed environment, such that pressure increases as ammonia and carbon dioxide is generated. In another embodiment a pressure release valve may be employed to maintain a constant pressure.

In embodiments the heating is carried out at a pressure of at least 100, 130, 150, 200, 250, 300, 500, 1000, 2000, 3000, 4000, 5000, 10000 or 15000 kPa and/or no more than 200000, 150000, 100000, 50000, 10000, 5000, 4000, 3000, 2000, 1500, 1000, 800, 600, 400, 200 or 100 kPa. In a particular embodiment the heating takes place at a pressure of 100 to 500 kPa or 100 to 300 kPa (abs).

In embodiments the heating is carried out below atmospheric pressure. In a series of such embodiments the heating is carried out at a pressure of no more than 99, 95, 90, 80 or 70 kPa and/or at least 10, 30 or 50 kPa.

In embodiments heating comprises heating the first portion of the aqueous urea to produce gaseous ammonia, carbon dioxide and water.

In embodiments heating comprises heating the portion of the aqueous solution of urea to generate ammonia and carbon dioxide in liquid water. A benefit of heating at elevated pressure is that the water in the aqueous urea solution may be kept liquid, rather than becoming a gas (steam), which encourages full decomposition of the urea.

In embodiments the heating takes place in the flow path. In one such embodiment the flow path comprises or constitutes a decomposition chamber. In embodiments the decomposition chamber may have a volume of at least 0.05, 0.1, 0.15, 0.2, 0.3 or 0.5 liters and/or no more than 2, 1.5, 1 or 0.5 liters. Ammonia can be corrosive so the flow path should be made from a material that can withstand ammonia, especially if heating is to take place there. In one embodiment the flow path is formed from stainless steel.

Cooling the mixture comprises cooling the mixture to form an aqueous solution of ammonium carbamate i.e. a liquid. In embodiments the mixture is cooled by means of a heat exchanger.

In embodiments the cooling takes place in the flow path. In one such embodiment the flow path comprises a chiller, e.g. a condenser having a coolant fluid flowing therein. Additionally or alternatively, the flow path may comprise a pressure reducing valve e.g. a constant back pressure valve. Since enthalpy is constant over the valve, expansion of a gas forces a temperature drop. These are examples of forced cooling.

In embodiments the cooling comprises cooling the mixture of ammonia, carbon dioxide and water to a temperature of no more than 200, 150, 100, 50, 40 or 30° C. and/or at least 5, 10, 15, 20 or 25° C.

In embodiments the cooling is carried out at or above atmospheric pressure. Ambient and higher pressures bias the reaction towards the formation of ammonium carbamate. In one embodiment cooling may be carried out in a sealed environment, such that pressure reduces as aqueous ammonium carbamate is generated. In another embodiment a pressure release valve may be employed to maintain a constant pressure.

In embodiments the heating and the cooling take place in the flow path.

In embodiments the heating takes place in the flow path and the cooling takes place in the second reservoir.

In embodiments each of the heating and the cooling takes place in the second reservoir. In one such embodiment the second reservoir comprises a heat exchanger which heats the aqueous urea solution and cools the resulting mixture comprising ammonia, carbon dioxide and water, thereby producing aqueous ammonium carbamate.

In embodiments of the invention, a hydrolysis catalyst is employed to assist with the conversion of aqueous urea to aqueous ammonium carbamate. It will be understood that the ammonium carbamate is stored in the second reservoir before being introduced into the exhaust stream.

In embodiments of the invention, no hydrolysis catalyst is employed to convert urea to ammonium carbamate. The use of a hydrolysis catalyst complicates the apparatus and increases cost.

Ammonia can be corrosive so the second reservoir should be made from a material that can withstand ammonia, especially if heating or cooling is to take place there. In one embodiment the second reservoir is formed from stainless steel.

In embodiments the process is carried out to produce no more than 500, 400, 300, 200, 100, 80, 60, 40, 30, 20 or 10 g of ammonium carbamate solution per minute. Such quantities may not be useful in a commercial process, but may provide sufficient ammonium carbamate for a cold-start reduction of NOx.

Apparatus

According to a third aspect of the present invention there is provided apparatus for delivering first and second compositions to an exhaust stream, the apparatus comprising a first reservoir for storing a first composition and means for delivering a first composition from the first reservoir to an exhaust stream;
a second reservoir for storing a second composition and means for delivering a second composition from the second reservoir to an exhaust stream;
a flow path from the first reservoir to the second reservoir, the flow path and the second reservoir being configured to convert the first composition into the second composition.

It will be understood that the apparatus may be employed to convert aqueous urea solution (a first composition) to aqueous ammonium carbamate solution (a second composition) in accordance with the second aspect of the invention and thereby reduce NOx in accordance with the first aspect of the invention. Hence the comments above in relation to the first and second aspects of the invention may apply here.

In embodiments the means for delivering the first composition to an exhaust stream and/or the means for delivering the second composition to an exhaust stream comprises an injector. In embodiments a single injector is employed to deliver the first composition and the second composition to an exhaust stream.

Control Unit

In embodiments the apparatus additionally comprises a programmable control unit (ECU). The ECU may be programmed to deliver the first composition and/or the second composition to the exhaust stream in accordance with specific criteria. In one such embodiment the ECU controls one or more valves and/or pumps which limit the release of the first and/or second compositions into the exhaust stream. In one such embodiment the ECU controls one or more valves and/or pump which meter the transfer of the first composition into the flow path.

Reduction Chamber

In embodiments the apparatus additionally comprises a reduction chamber having a selective catalytic reduction (SCR) catalyst therein for reducing NOx in an exhaust stream. The reduction chamber will be located downstream of the first and second reservoirs.

The reduction chamber may be a conventional reduction chamber having an SCR catalyst (e.g. $WTiO_2$) therein. In embodiments the SCR catalyst comprises a wall flow catalyst e.g. a wall flow $WTiO_2$ catalyst. This is useful for filtration of diesel particulates.

Ammonia Oxidation Catalyst (AMOX)

In embodiments the apparatus additionally comprises an ammonia oxidation catalyst (AMOX) located downstream from the reduction chamber, to oxidize any excess ammonia.

Sensors

In embodiments the apparatus comprises a temperature sensor located in the exhaust stream to determine the exhaust stream temperature. This information can be relayed to the ECU.

In embodiments the apparatus comprises at least one NOx sensor. In one embodiment a NOx sensor is located upstream of the first reservoir (and reduction chamber). The NOx sensor can then provide information to the ECU to determine whether NOx reduction is required. In one embodiment a further NOx sensor is located downstream of the reduction chamber. The NOx sensor can provide information to determine the efficiency of the reduction.

In embodiments the apparatus comprises at least one ammonia sensor. In one such embodiment the ammonia sensor is located downstream from the reduction chamber (and optional AMOX) to determine whether excess ammonia is present.

Fitting and Retro-Fitting

The invention also resides in fitting the apparatus of the third aspect to a combustor, e.g. a vehicle or generator. The apparatus may be fitted when the combustor (e.g. vehicle or generator) is manufactured or at a later date (retro-fitting). The system requires very little engine design alteration whilst dramatically reducing the total NOx output. Increased NOx reduction capability can also benefit other regulated emissions allowing an engine to operate at a more efficient condition reducing both $CO_2$ and PM. The invention also resides in a combustor configured for the process of the first aspect; configured for the process of the second aspect; or comprising the apparatus of the third aspect. The invention also resides in a system comprising such a combustor e.g. a vehicle or generator.

In accordance with a fourth aspect of the invention, there is provided an apparatus for reducing nitrogen oxides (NOx) in an exhaust stream comprising nitrogen oxides, the apparatus comprising:
  a first source of a first composition comprising urea and water, the first source comprising a first reservoir for the first composition;
  a second source of a second composition comprising ammonium carbamate, the second source comprising a second reservoir for the second composition;
  a passage for the exhaust stream;
in which the apparatus comprises a flow control apparatus arranged to:
  selectively couple the second source to the passage to introduce the second composition into the exhaust stream; and
  selectively couple the first source to the passage to introduce the first composition into the exhaust stream.

The first composition is typically an aqueous solution of urea. In one such embodiment the first composition consists essentially of urea and water, e.g. AdBlue® (aqueous urea solution, standardised to AUS32, also known as a diesel engine fuel (DEF)). There is already an existing market acceptance for AdBlue® as an ammonia precursor and an extensive distribution network.

In one series of embodiments the first composition comprises at least 5, 10, 15, 20, 25, 30, 35, 40, 45 or 50 wt % urea/or no more than 80, 70, 60, 50, 40, 30, 20 or 10 wt % urea. The balance may be water.

In one embodiment the first composition comprises 30 to 35 wt %, 31 to 34 wt %, 32 to 33 wt % or approximately 32.5% urea, with the balance being water. The commercially available product AdBlue® consists of 32.5 wt % urea and 67.5 wt % water. This is said to be correspond closely to a eutectic mixture. In a preferred embodiment the first composition is AdBlue®.

The first and/or second compositions may be introduced into the exhaust stream in any conventional way e.g. by injection. As such, the apparatus may comprise means for delivering the first composition to an exhaust stream and/or means for delivering the second composition to an exhaust stream, which may in both cases comprise an injector. In embodiments a single injector is employed to deliver the first composition and the second composition to the exhaust stream.

In embodiments the second composition is an aqueous composition i.e. a solution of the ammonium carbamate in water. In embodiments the first composition consists of ammonium carbamate and water, optionally with dissolved ammonia.

In embodiments the second composition comprises at least 5, 10, 15, 20, 25, 30, 35, 40, 45 or 50 wt % ammonium carbamate and/or no more than 70, 60, 50, 40, 45, 30, 35, 20 or 10 wt % ammonium carbamate. The balance may be water.

In embodiments the second composition comprises from 25 to 45 wt %, from 30 to 44 wt %, from 33 to 43 wt % or approximately 42 wt % ammonium carbamate. When the ammonium carbamate is produced in situ from AdBlue® (32.5 wt % urea and 67.5 wt % water), the resulting ammonium carbamate solution comprises approximately 42.25 wt % ammonium carbamate (assuming complete conversion).

The second composition may be introduced into the exhaust stream in any conventional way e.g. by injection.

The suitability of the first and second compositions for reducing NOx depends on the temperature of the exhaust stream. The first composition (comprising urea) is more appropriate at higher temperatures and the second composition (comprising ammonium carbamate) is more appropriate at lower temperatures.

In embodiments, the flow control apparatus is arranged so as to couple the second source to the passage when the exhaust stream has a temperature below a threshold temperature, and to couple the first source to the passage when the exhaust stream has a temperature above the threshold temperature.

The skilled person can select the threshold temperature depending on his needs. The skilled person will appreciate that the threshold temperature can be selected depending on a number of factors familiar to him including the relative financial costs of the first and second compositions (which may vary over time), the amount of NOx and other emissions that he is willing to tolerate, the quantities of the first and second compositions that are available, the amount of deposition (from urea) that he is willing to tolerate, any additional components present in the first and second compositions, and the operating conditions.

For example, an exhaust stream temperature of at least 350° C. is desirable for full decomposition of AdBlue® to form ammonia and deposits are likely to form when the temperature is less than 190° C. Therefore, if AdBlue® is employed as the first composition the skilled person may select a threshold temperature of at least 250° C.

In one series of embodiments the threshold temperature is at least 100, 150, 200, 230, 250, 270, 300, 350 or 400° C. and/or no more than 1000, 800, 600, 400, 200 or 100° C. In a particular embodiment, the threshold temperature is selected from the range 200 to 400° C.

The apparatus may be arranged such that only the first composition or only the second composition is introduced into the exhaust stream at a given temperature i.e. the threshold temperature can act as a cut-off. In some embodiments the first composition is only introduced into the exhaust stream when the exhaust stream has a temperature at or above the threshold temperature. In some embodiments the second composition is only introduced into the exhaust stream when the exhaust stream has a temperature below the threshold temperature.

Alternatively the apparatus may be arranged such that both of the first composition and the second composition are introduced into the exhaust stream at a given temperature.

In some circumstances a gradual change from the second composition to the first composition as the temperature of the exhaust stream increases may be beneficial. Such an approach would avoid the risk of no reducing agent being available for even a short period of time.

In embodiments the first composition is only introduced into the exhaust stream when the exhaust stream has temperature (the exhaust stream temperature)
(i) at or above the threshold temperature; or
(ii) no more than 100, 50, 20 or 10° C. below the threshold temperature.

In embodiments the second composition is only introduced into the exhaust stream when the exhaust stream has temperature (the exhaust stream temperature)
(i) below the threshold temperature; or
(ii) no more than 100, 50, 20 or 10° C. above the threshold temperature.

It will be understood that it is necessary to know the temperature of the exhaust stream in order to determine whether the first composition and/or the second composition should be introduced; as such, the apparatus may comprise a temperature sensor coupled to the flow control apparatus. Alternatively, the flow control apparatus may be arranged to infer an approximate temperature from the conditions.

The first reservoir may correspond to a conventional AdBlue® tank on a vehicle. In embodiments the first reservoir has a volume of no more than 500, 200, 100, 50, 30 or 20 liters and/or at least 10, 20 or 50 liters. In embodiments the first reservoir has a volume of 10 to 100 liters. The first reservoir may contain the first composition.

The second reservoir typically stores the aqueous ammonium carbamate that is produced. Hence a portion of the aqueous solution of urea is transferred from the first reservoir, along the flow path, to the second reservoir and may be converted to ammonium carbamate on the way or in the second reservoir. As discussed above, it may not be safe or practical to store large volumes of aqueous ammonium carbamate. In embodiments the second reservoir has a volume of no more than 10, 8, 5, 3, 2, 1 or 0.5 liters and/or at least 0.05, 0.1, 0.2, 0.5, or 1 liters. The second reservoir may contain the second composition.

In embodiments the first reservoir has a greater volume than the second reservoir. In embodiments, the volume of the first reservoir is at least 5, 10, 20, 50 or 100 times greater than the volume of the second reservoir.

In embodiments the apparatus is arranged to prepare the ammonium carbamate from a precursor. The precursor may be the first composition. As such, the first reservoir may be coupled to the second reservoir through a flow path, the flow path and the second reservoir together forming a reaction path being configured to convert the first composition into the second composition.

The reaction path may be provided with heating means arranged to heat fluid flowing through a heating part of the reaction path. Typically, this will heat the first composition as it passes through the heating part of the reaction path, in order to encourage the conversion of the first composition to the second composition. In embodiments the heating means may be an electrical heater. Alternatively or additionally, the heating means may comprise a heat-exchanger, e.g. a heat-exchanger in communication with an exhaust stream, engine coolant or an electrical heater. It is an advantage of the present process that the ammonium carbamate can be produced when an exhaust stream is hot, using energy that would otherwise be wasted.

The heating means may be arranged to heat the contents of the heating part of the reaction path to a temperature of at least 100, 150, 200, 250, 300, 350 or 400° C. and/or no more than 1000, 800, 600 or 500° C. Higher temperatures increase the rate of ammonium carbamate production.

The heating part of the reaction path may be arranged to withstand and/or achieve heating at or above atmospheric pressure. The heating part of the reaction path may provide a sealed environment, such that pressure increases as ammonia and carbon dioxide is generated. In another embodiment the heating part of the reaction path may comprise a pressure release valve arranged so as to maintain a constant pressure in the heating part of the reaction path.

The heating part of the reaction path may be arranged to withstand and/or achieve a pressure of at least 100, 130, 150, 200, 250, 300, 500, 1000, 2000, 3000, 4000, 5000, 10000 or 15000 kPa and/or no more than 200000, 150000, 100000, 50000, 10000, 5000, 4000, 3000, 2000, 1500, 1000, 800, 600, 400, 200 or 100 kPa. In a particular embodiment the heating part of the reaction path may be arranged to withstand and/or achieve a pressure of 100 to 300 kPa.

The heating part of the reaction path may be arranged to withstand and/or achieve heating at below atmospheric pressure. In a series of such embodiments the heating part of the reaction path may be arranged to withstand and/or achieve pressure of no more than 99, 95, 90, 80 or 70 kPa and/or at least 10, 30 or 50 kPa.

In embodiments, the heating means is arranged so as to heat the aqueous solution of urea to generate ammonia and carbon dioxide in liquid water. A benefit of heating at elevated pressure is that the water in the aqueous urea solution may be kept liquid, rather than becoming a gas (steam), which encourages full decomposition of the urea.

In one embodiment, the heating part of the reaction path comprises a decomposition chamber, to which the heating means may be thermally coupled. In embodiments the decomposition chamber may have a volume of at least 0.05, 0.1, 0.15, 0.2, 0.3 or 0.5 liters and/or no more than 2, 1.5, 1 or 0.5 liters. Ammonia can be corrosive so the heating part of the reaction path should be made from a material that can withstand ammonia, especially if heating is to take place there. In one embodiment the heating part of the reaction path is formed from stainless steel.

A second, cooling part, of the reaction path may be provided with cooling means arranged to cool material passing through the cooling part of the reaction path; the material will typically be a mixture of ammonia, carbon dioxide and water output the heating part of the reaction path. In one such embodiment, the cooling means comprises a chiller, e.g. a condenser having a coolant fluid flowing therein. Additionally or alternatively, the cooling means may comprise a pressure reducing valve e.g. a constant back pressure valve. Since enthalpy is constant over the valve, expansion of a gas forces a temperature drop.

In embodiments the cooling means is arranged to cool the material passing through the cooling part of the reaction path to a temperature of no more than 200, 150, 100, 50, 40 or 30° C. and/or at least 5, 10, 15, 20 or 25° C.

The cooling means may be arranged such that the cooling is carried out at or above atmospheric pressure. Ambient and higher pressures bias the reaction towards the formation of ammonium carbamate. The cooling part of the reaction path may provide a sealed environment, such that pressure reduces as aqueous ammonium carbamate is generated. In another embodiment the cooling part of the reaction path may comprise a pressure release valve in the cooling part to maintain a constant pressure.

Typically, the heating part of the reaction path comprises the flow path, and the cooling part of the reaction path comprises the second reservoir. As such, the heating means may be thermally coupled to the flow path, and the cooling means may be thermally coupled to the second reservoir.

In other embodiments, both the heating and cooling parts of the reaction path comprise the second reservoir. In one such embodiment the second reservoir comprises a heat exchanger which heats the aqueous urea solution and cools the resulting mixture comprising ammonia, carbon dioxide and water.

Ammonia can be corrosive so the second reservoir should be made from a material that can withstand ammonia, especially if heating or cooling is to take place there. In one embodiment the second reservoir is formed from stainless steel.

The flow control apparatus may be arranged so as to deliver the first composition and/or the second composition to the exhaust stream in accordance with specific criteria. The flow control apparatus may comprise at least one valve and/or pump which limit the release of the first and/or second compositions into the exhaust stream. Each valve and/or pump may be arranged to meter the transfer of the first composition into the flow path.

The urea solution and the ammonium carbamate solution each produce ammonia, which reduces NOx in the exhaust stream. In embodiments the passage comprises a reduction chamber having a selective catalytic reduction (SCR) catalyst therein.

In accordance with a fifth aspect of the invention, there is provided a combustor system, comprising a combustor having an exhaust output for combusted gasses, and the apparatus of the fourth aspect of the invention coupled to the exhaust output such that the combusted gasses pass through the passage.

The combustor may be an internal combustion engine. The combustor may be stationary (e.g. a utility boiler or diesel generator) or mobile (e.g. that of a vehicle). The process is especially useful for on highway and off highway vehicles which currently employ SCR reduction of NOx.

In accordance with a sixth aspect of the invention, there is provided a vehicle having the combustor of the fifth aspect of the invention, wherein the combustor is an internal combustion engine of the vehicle. Typically, the vehicle will be a wheeled vehicle, such as a road vehicle, and the internal combustion engine will be arranged to power at least one wheel of the vehicle.

Embodiments of the invention will now be described with reference to the following figures in which.

Figure 1:
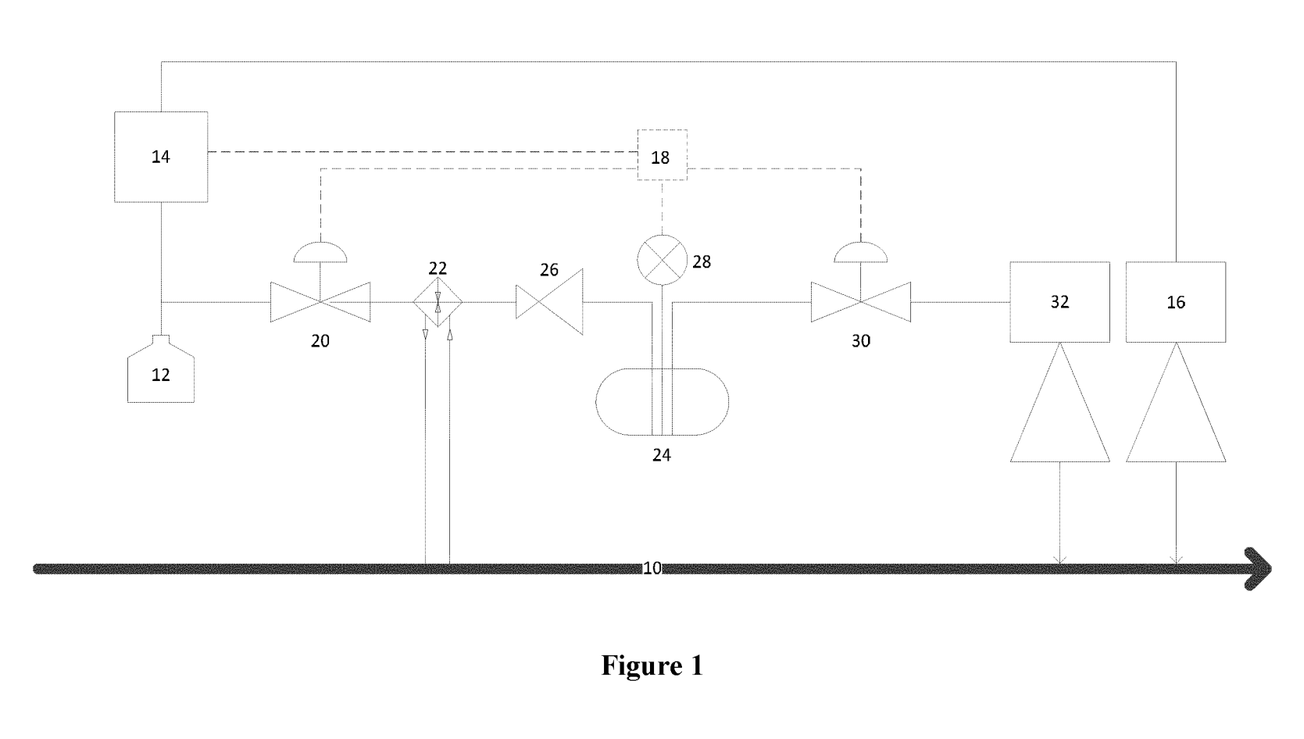
FIGS. 1 to 6 are schematic diagrams of systems in accordance with embodiments of the invention.

Referring to FIG. 1 there is shown an exhaust stream 10 containing NOx that flows from left (upstream) to right (downstream), as indicated by an arrow. The system comprises a first reservoir 12 containing aqueous urea (e.g. an AdBlue® tank). The aqueous urea is metered into the exhaust stream 10 via a flow control apparatus comprising a conventional delivery system 14, which comprises an injector 16. An ECU 18 is programmed with a given threshold temperature (e.g. 300° C.), such that the aqueous urea is injected into the exhaust stream 10 when the exhaust stream temperature is at or above the threshold temperature. The aqueous urea decomposes in the exhaust stream 10 to generate ammonia and carbon dioxide which passes downstream to a reduction chamber (not shown) having a selective catalytic reduction catalyst therein. The ammonia reduces the NOx in the reduction chamber.

A portion of the aqueous urea solution is released from the first reservoir 12 and transferred via a first valve 20 (also part of the flow control apparatus) to a decomposition heat exchanger 22 (also known as a decomposition chamber). The decomposition heat exchanger 22 is in communication with the exhaust stream 10 and uses heat from the exhaust stream 10 to decompose the aqueous urea solution to form carbon dioxide and ammonia. The mixture comprising water, carbon dioxide and ammonia is then transferred to a sealed reservoir 24 by means of a pressure reducing valve 26. The mixture is cooled by passing through the valve 26 and also radiates heat from the reservoir 24, thereby generating ammonium carbamate solution. The sealed reservoir 24 is at lower pressure that the decomposition heat exchanger 22 and its pressure is measured by means of a pressure sensor 28. Conversion of aqueous urea to ammonium carbamate is controlled by the ECU 18, which opens the flow valve 20 when required. The ammonium carbamate solution is transferred from the reservoir 24 via a valve 30 to an injector 32 and injected into the exhaust stream 10 when the exhaust stream temperature is below the threshold temperature. The ammonium carbamate solution decomposes to form ammonia and carbon dioxide which passes downstream to a reduction chamber where the ammonia reduces NOx.

Figure 2:
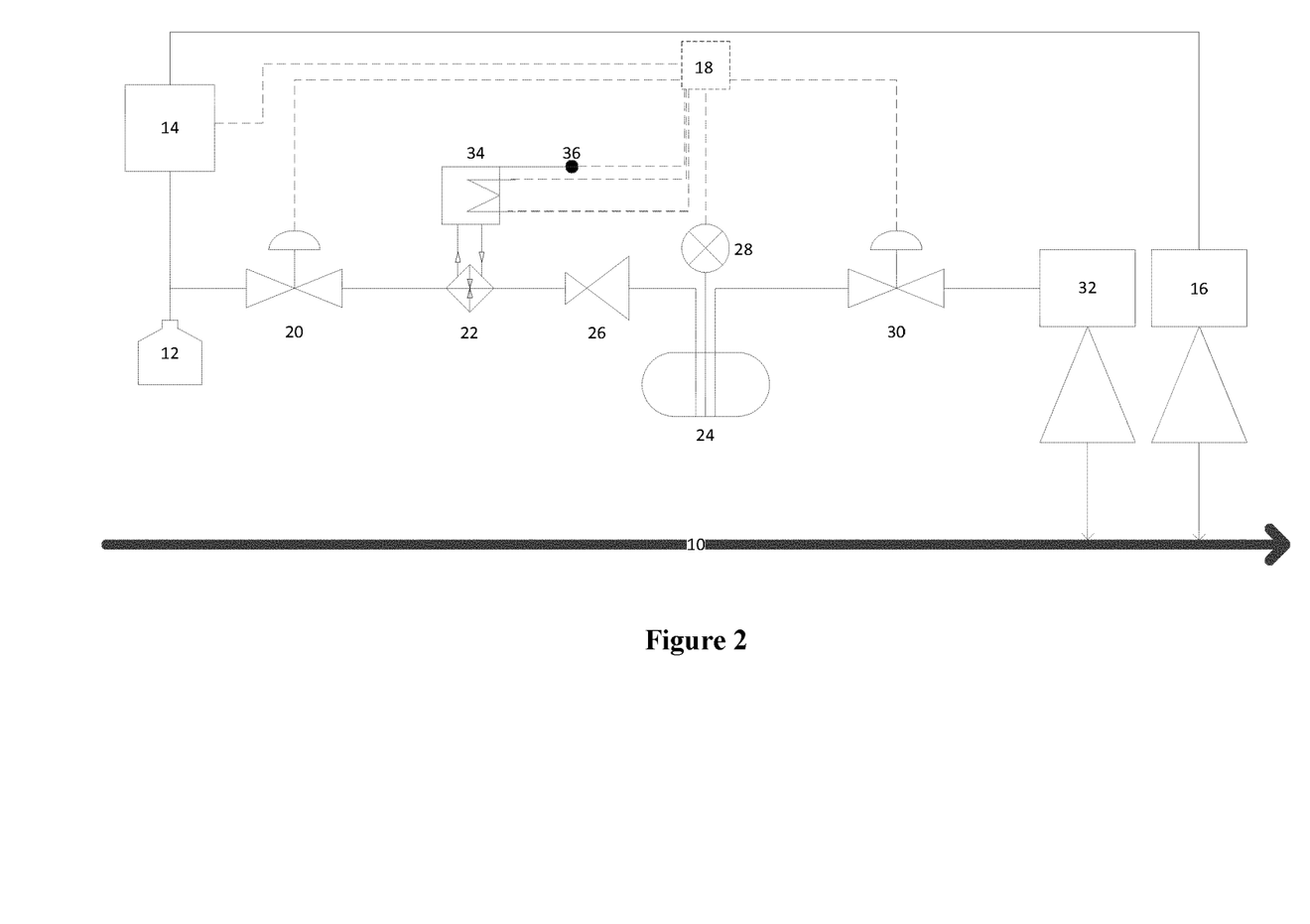

Referring to FIG. 2 there is shown another exhaust system in accordance with an embodiment of the invention. The system is similar to that shown in FIG. 1 except that the decomposition heat exchanger 22 is in communication with an electrical heater 34, rather than using heat from the exhaust stream 10. The temperature of the heater 34 is measured by a temperature sensor 36, and controlled by the ECU 18.

Figure 3:
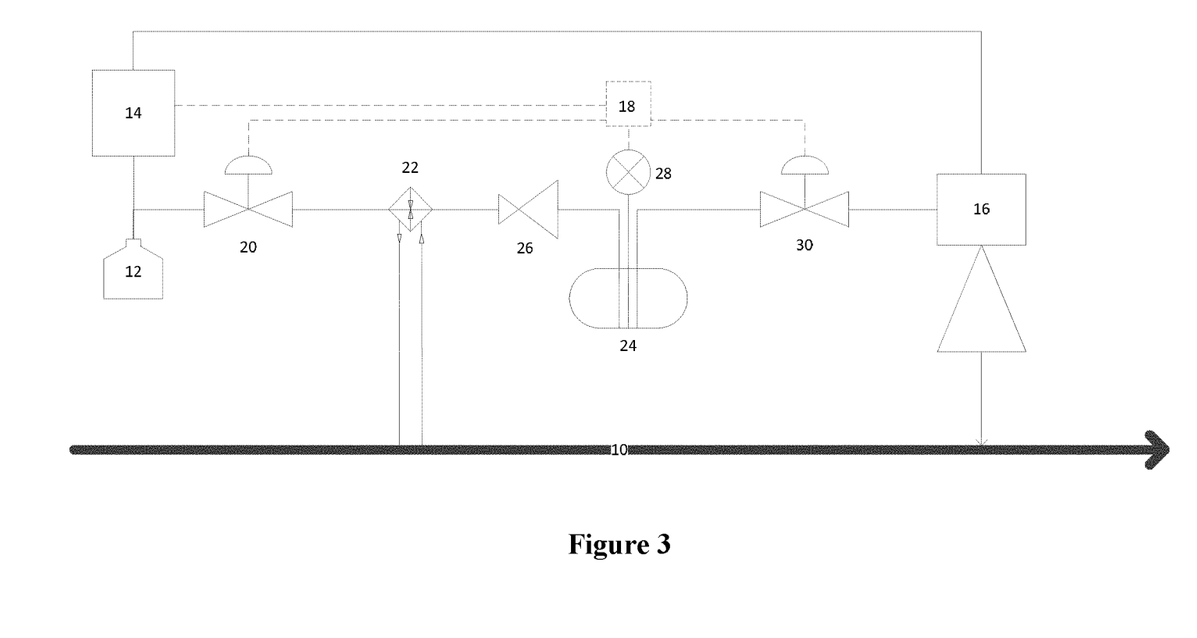

The system in FIG. 3 is similar to the system of FIG. 1 except that it employs the injector 16 of the conventional delivery system 14 (e.g. AdBlue® delivery system) to deliver the ammonium carbamate, rather than a dedicated ammonium carbamate injector. Hence, a second injector is not required and the apparatus is more compact.

Figure 4:
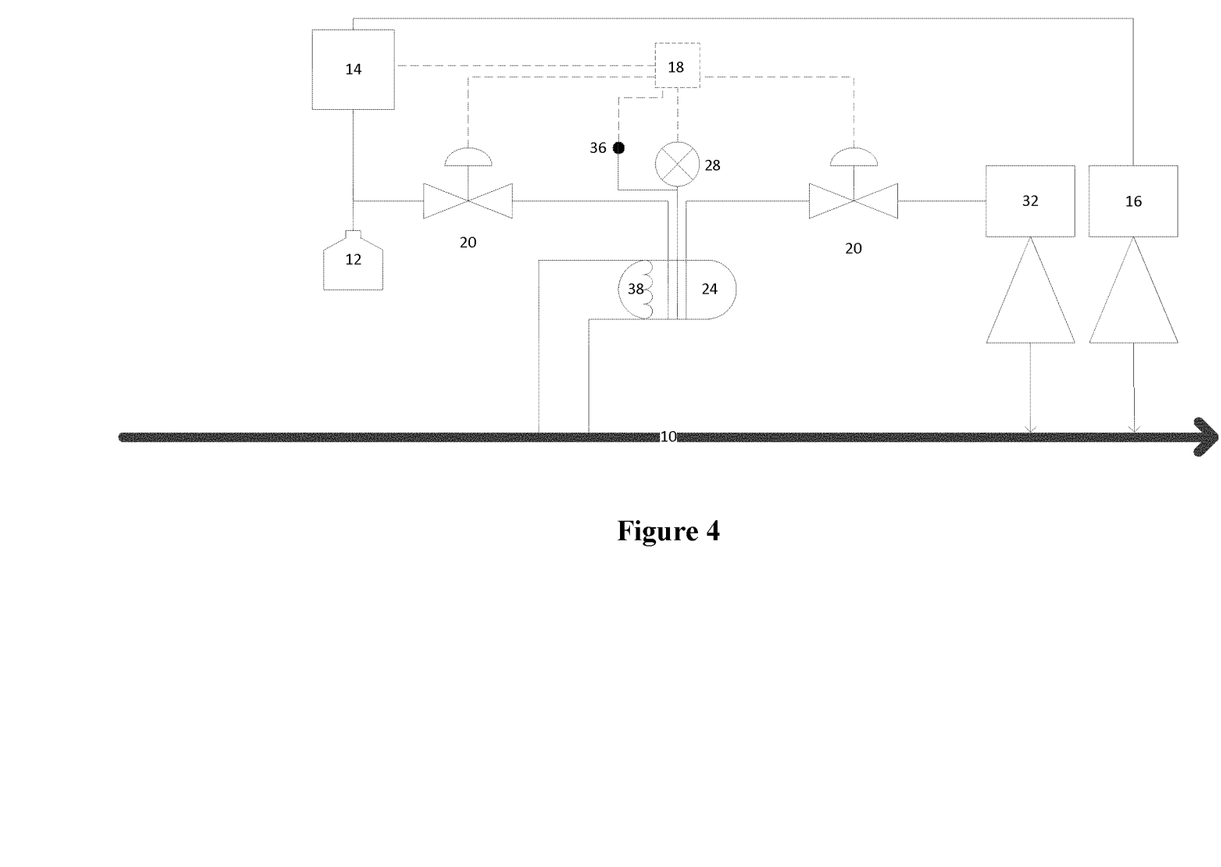

The system of FIG. 4 is similar to that in FIG. 1 except that a heat exchanger 38 is located in the sealed reservoir 24, rather than in the flow path between the reservoirs 12, 24. A portion of the aqueous urea solution is transferred from the first reservoir 12 though the valve 20 to the second reservoir 24. The heat exchanger 38 uses heat from the exhaust system to heat the aqueous urea solution to form ammonia and carbon dioxide and subsequently cools the mixture comprising water, ammonia and carbon dioxide to form ammonium carbamate, which remains in the reservoir 24. The temperature and pressure is measured by sensors 36, 28 and controlled by the ECU 18.

Figure 5:
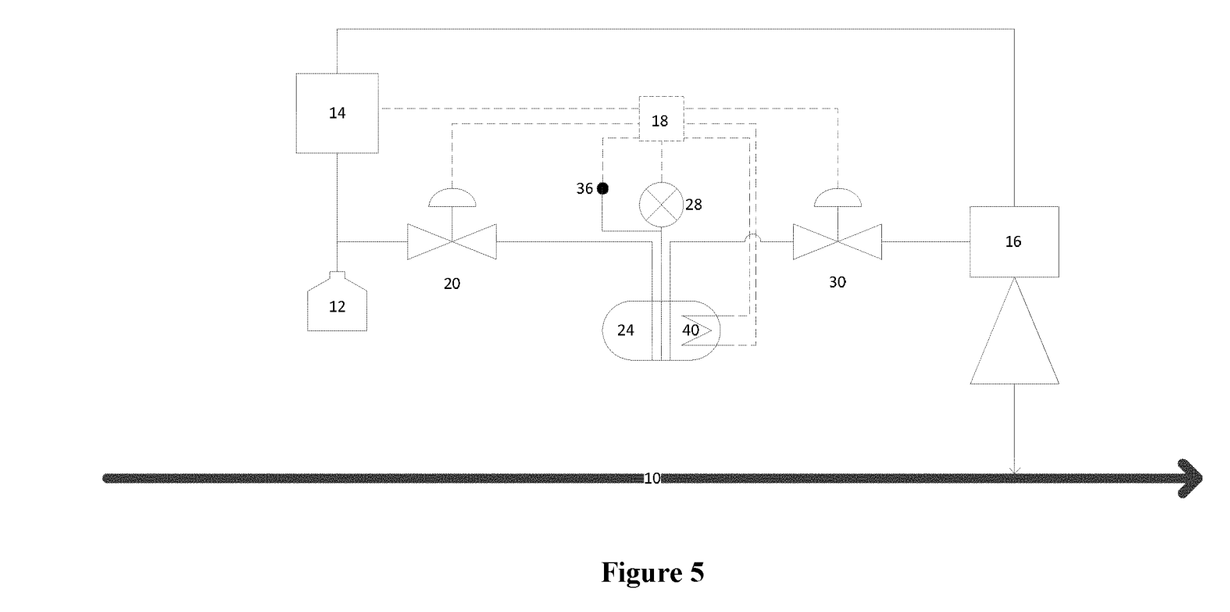

The system of FIG. 5 is similar to that of FIG. 4 except that the reservoir 24 contains an electrical heater 40 instead of a heat exchanger. Cooling takes place by radiation from the reservoir 24. Alternatively a piezo electrical heater is employed that can also cool the mixture. Furthermore, the conventional injector 16 is employed to deliver both the urea solution and the ammonium carbamate to the exhaust stream 10, thereby making the apparatus more compact.

Figure 6:
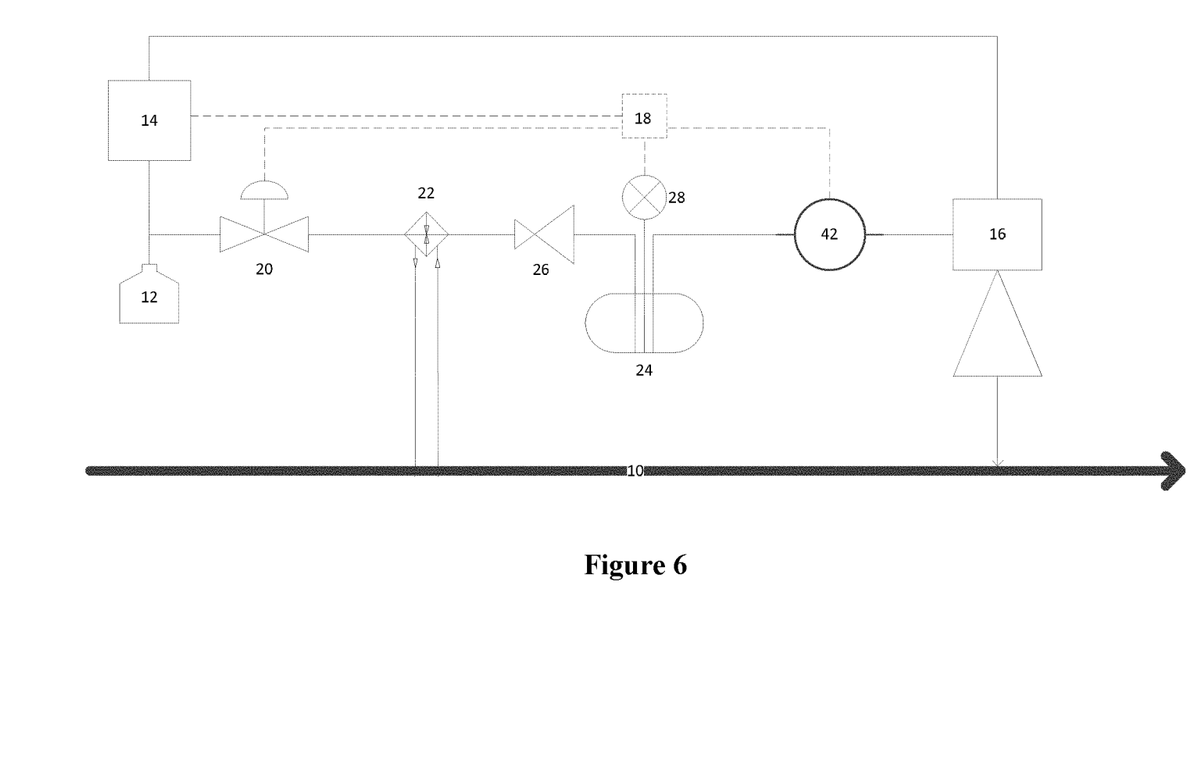

The system of FIG. 6 is similar to FIG. 3 except that a dosing pump 42 is employed in place of the second flow valve 30. The dosing pump 42 transfers ammonium carbamate to the injector 16. The dosing pump 42 ensures that the ammonium carbamate is transferred consistently, even when the pressure in the reservoir 24 is low. A dosing pump is also useful if atomisation from the injector 16 is desired.

Figure 7:
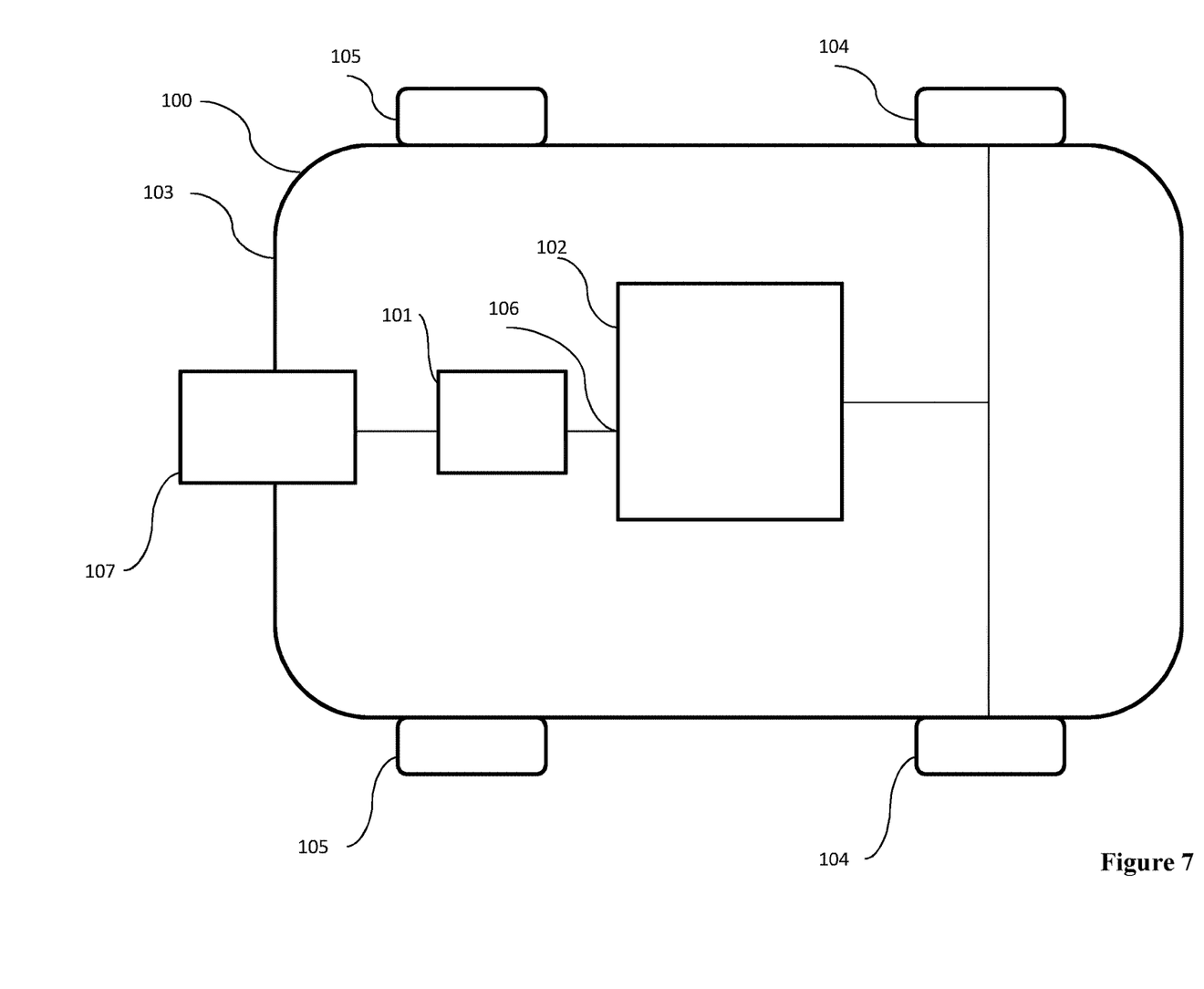
FIG. 7 is a schematic diagram of a vehicle in accordance with an embodiment of the invention.

FIG. 7 shows a vehicle 100 which can be used with the exhaust system 101 of any of the previous embodiments. In this embodiment, the vehicle is an automobile, but it could be any automotive vehicle from a motorbike through automobiles of any type through to large commercial vehicles such as trucks and busses, to large industrial vehicles such as earth-movers and other construction vehicles. The vehicle could alternatively be a train, or a marine vessel, in which case the engine described below would drive a propeller rather than wheels.

This vehicle has an internal combustion engine 102 mounted in a vehicle body 103. The vehicle body 103 supports two driven wheels 104 driven by the internal combustion engine 102 and two non-driven wheels 105.

The internal combustion engine has an output port 106 for exhaust gasses generated by the internal combustion engine. Such gasses are passed to the exhaust system 101, which can be as described with respect to any of FIGS. 1 to 6. The gasses pass through the exhaust stream 10 of the exhaust system 101. Thus, the exhaust system 101 reduces the levels of NOx in the exhaust gasses.

The treated exhaust gasses are then passed to an exhaust pipe 107 of the vehicle to be exhausted to the surrounding atmosphere.

Figure 8:
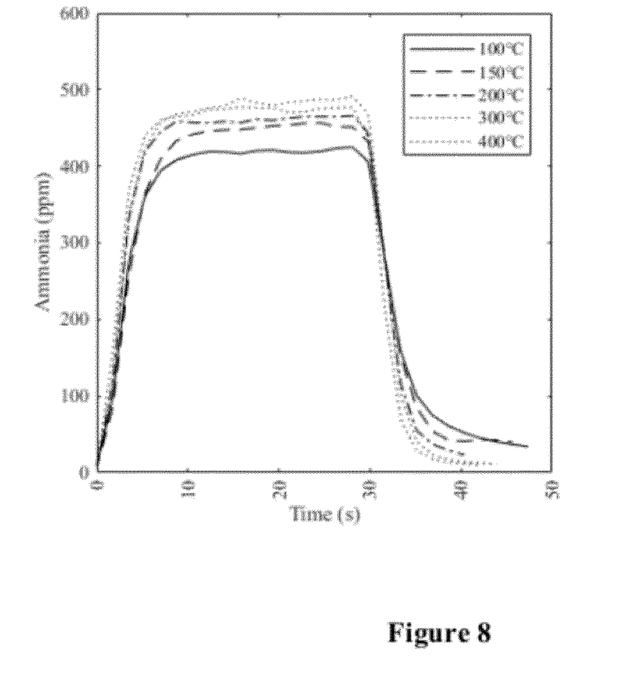
FIG. 8 is a graph showing ammonia generation at varying temperatures downstream of injection of aqueous ammonium carbamate.

FIG. 8 demonstrates the decomposition of ammonium carbamate at 100° C. (solid line), 150° C., 200° C., 300° C. and 400° C. (dotted line). Full ammonia release is demonstrated quickly.

Figure 9:
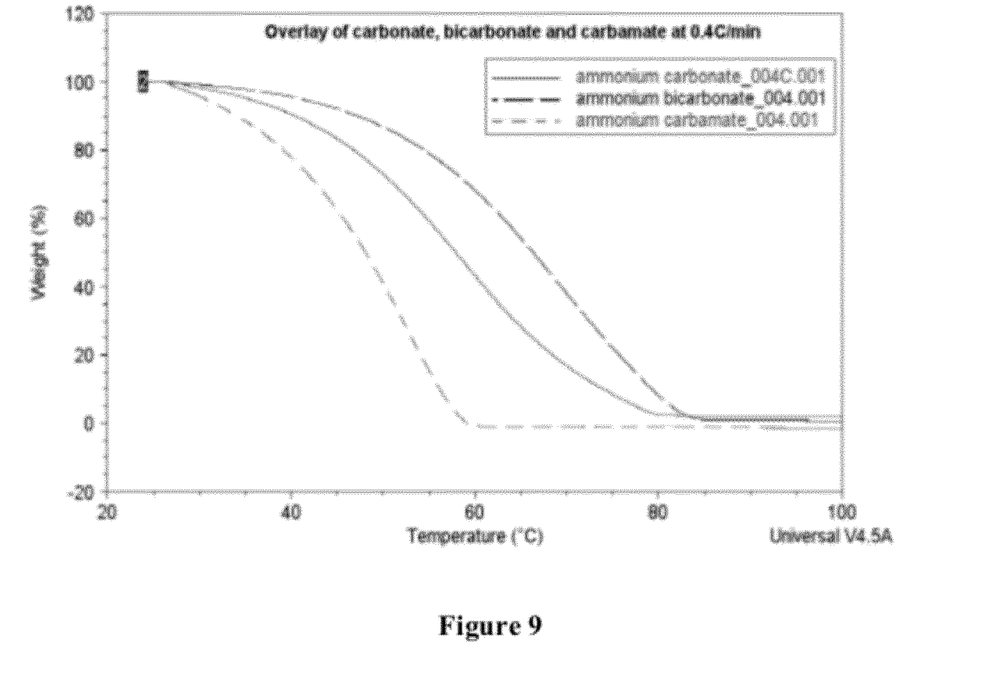
FIG. 9 shows the decomposition on heating of ammonium carbonate, ammonium bicarbonate and ammonium carbamate.

FIG. 9 compares the decomposition of ammonium carbamate with the decomposition of ammonium carbonate and ammonium bicarbonate, with increasing (negative) gradient of each graph showing an increased rate of decomposition. Ammonium carbamate demonstrates a rapid rate of decomposition from 50° C., ammonium carbonate from 60° C. and ammonium bicarbonate from 70° C. Both ammonium carbonate and bicarbonate demonstrate slower rates than ammonium carbamate. Both ammonium carbonate and bicarbonate demonstrate slower rates than carbamate.

The invention claimed is:

1. A process for reducing nitrogen oxides in an exhaust stream, the process comprising providing a first reservoir having the first composition therein, the first composition comprising aqueous urea;

transferring a portion of the first composition along a flow path, the flow path being in communication with a second reservoir;

heating the portion of the first composition to produce a mixture comprising ammonia, carbon dioxide and water; the heating taking place in the flow path or in the second reservoir;

cooling the mixture to generate a second composition, the second composition comprising aqueous ammonium carbamate and the cooling taking place in the flow path or in the second reservoir;

introducing the second composition from the second reservoir into an exhaust stream comprising nitrogen oxides.

2. The process of claim 1, wherein the first composition is not introduced into the exhaust stream.

3. The process of claim 1, wherein the second composition is introduced into the exhaust stream when the exhaust stream has a temperature below a threshold temperature and the first composition is introduced into the exhaust stream when the exhaust stream has a temperature at or above the threshold temperature.

4. The process of claim 3, wherein (i) the threshold temperature is at least 250° C.; and/or (ii) the threshold temperature is no more than 400° C.

5. The process of claim 1 wherein (i) the first composition comprises at least 20 wt % urea and/or (ii) the second composition comprises at least 20 wt % ammonium carbamate.

6. The process of claim 1, wherein the exhaust stream is (i) a vehicle exhaust stream or (ii) a stationary generator exhaust stream.

7. The process of claim 1, wherein (i) the volume of the first reservoir is greater than the volume of the second reservoir; and/or (ii) the second reservoir has a volume of no more than 5 liters; and/or (iii) the second reservoir has a volume of at least 0.1 liters.

8. The process of claim 1, wherein (i) the portion of the first composition is heated by means of a heat-exchanger in communication with the exhaust stream; and/or (ii) the cooling comprises passing the ammonia and carbon dioxide through a pressure reducing valve; and/or (iii) the cooling comprises cooling the mixture with a heat exchanger.

9. An apparatus for reducing nitrogen oxides (NOx) in an exhaust stream comprising nitrogen oxides, the apparatus comprising:

a first source of a first composition comprising urea and water, the first source comprising a first reservoir for the first composition;

a second source of a second composition comprising ammonium carbamate, the second source comprising a second reservoir for the second composition;

a passage for the exhaust stream;

in which the apparatus comprises a flow control apparatus arranged to:

selectively couple the second source to the passage to introduce the second composition into the exhaust stream; and selectively couple the first source to the passage to introduce the first composition into the exhaust stream.

10. The apparatus of claim 9, in which the first reservoir has a volume of 10 to 100 liters.

11. The apparatus of claim 9, in which the second reservoir has a volume of no more than 10, 8, 5, 3, 2, 1 or 0.5 liters but at least 0.05, 0.1, 0.2, 0.5, or 1 liters.

12. The apparatus of claim 9, in which the flow control apparatus is arranged so as to couple the second source to the passage when the exhaust stream has a temperature below a threshold temperature, and to couple the first source to the passage when the exhaust stream has a temperature above the threshold temperature.

13. The apparatus of claim 9, comprising means for delivering the first composition to an exhaust stream and means for delivering the second composition to the exhaust stream in the passage.

14. The apparatus of claim 13, comprising a single injector arranged to deliver both the first composition and the second composition to the exhaust stream.

15. The apparatus of claim 9, in which the first reservoir is coupled to the second reservoir through a flow path, the flow path and the second reservoir together forming a reaction path being configured to convert the first composition into the second composition.

16. The apparatus of claim 15, in which the reaction path is provided with heating means arranged to heat fluid flowing through a heating part of the reaction path.

17. The apparatus of claim 15, in which a cooling part of the reaction path is provided with cooling means arranged to cool material passing through the cooling part of the reaction path.

18. The apparatus of claim 17, in which the reaction path is provided with heating means arranged to heat fluid flowing through a heating part of the reaction path and the heating part of the reaction path comprises the flow path, and the cooling part of the reaction path comprises the second reservoir.

19. A combustor system, comprising a combustor having an exhaust output for combusted gasses, and the apparatus of claim 9 coupled to the exhaust output such that the combusted gasses pass through the passage.

20. The combustor system of claim 19, in which the combustor is an internal combustion engine.

* * * * *